US007754248B2

(12) United States Patent
Seiberg et al.

(10) Patent No.: US 7,754,248 B2
(45) Date of Patent: Jul. 13, 2010

(54) INGESTIBLE COMPOSITIONS CONTAINING EXTRACTS

(75) Inventors: Miri Seiberg, Princeton, NJ (US); Violetta Iotsova Stone, Robbinsville, NJ (US); Renbin Zhao, Plainsboro, NJ (US); Elizabeth Bruning, Somerset, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 11/387,892

(22) Filed: Mar. 23, 2006

(65) Prior Publication Data
US 2006/0233898 A1 Oct. 19, 2006

Related U.S. Application Data

(63) Continuation-in-part of application No. 11/313,079, filed on Dec. 20, 2005, which is a continuation-in-part of application No. 11/248,465, filed on Oct. 12, 2005, which is a continuation-in-part of application No. 10/973,313, filed on Oct. 26, 2004.

(51) Int. Cl.
*A61K 36/00* (2006.01)
(52) U.S. Cl. .................................................. 424/725
(58) Field of Classification Search ........................ None
See application file for complete search history.

(56) References Cited

U.S. PATENT DOCUMENTS

| 3,777,755 | A | | 12/1973 | Groves |
| 4,521,411 | A | * | 6/1985 | Koloff ........................ 424/743 |
| 5,560,917 | A | | 10/1996 | Cohen |
| 5,814,031 | A | | 9/1998 | Mooney et al. |
| 6,228,387 | B1 | | 5/2001 | Borod |
| 6,342,208 | B1 | | 1/2002 | Hyldgaard et al. |
| 2002/0015726 | A1 | | 2/2002 | Aledo |
| 2002/0132021 | A1 | | 9/2002 | Raskin et al. |
| 2003/0180395 | A1 | | 9/2003 | Bueter |
| 2004/0131660 | A1 | | 7/2004 | Lange et al. |
| 2004/0175439 | A1 | | 9/2004 | Cyr |
| 2006/0165817 | A1 | | 7/2006 | Seiberg et al. |
| 2006/0233898 | A1 | | 10/2006 | Seiberg |

FOREIGN PATENT DOCUMENTS

| CN | 1 720 943 A | | 1/2006 |
| EP | 1238402 A2 | | 9/2002 |
| FR | 2 790 669 A | | 9/2000 |
| FR | 2 814 070 A | | 3/2002 |
| HU | 50033 T | | 12/1989 |
| JP | 2001206852 A | * | 7/2001 |
| JP | 2002205950 A | | 7/2002 |
| SU | 571269 A | * | 10/1977 |
| WO | WO 01/34099 A | | 5/2001 |
| WO | WO 02/069992 A | | 9/2002 |
| WO | WO 03/033007 A | | 4/2003 |
| WO | WO 2004046507 A | | 6/2004 |
| WO | 2006047470 A2 | | 5/2006 |
| WO | WO 2006/053415 A | | 5/2006 |
| WO | WO 2006/057755 A | | 6/2006 |
| WO | WO 2007/075750 A | | 7/2007 |

OTHER PUBLICATIONS

Drug Digests: Matricaria Chamomilla; URL<http://www.drugdigest.org/DD/DVH/HerbsWho/0,3923,4054%7CMatricaria+chamomilla,00.html> accessed May 4, 2007, one page.*
Stille, A. MD; Therapeutics and Materia Medica a Systematic Treatise of the Action and Uses of Medicinal Agents Including Their Description and History; Blanchard and Lea, Philadelphia, PA, 1860 pp. 127-128.*
Wood, H.C. MD LLD; Therapeutics; Its Principles and Practice; J.B. Lipincott Company, London, England, 1892, pp. 758-760.*
Parke, Davis & Company; Descriptive Catalogue of the Laboratory Products of Parke, Davis & Company; Parke, Davis & Company, Detroit, Michigan, 1894, p. 49.*
Phillipson, J. New Drugs From Nature—It Could Be Yew; Phytotherapy Research 13 (1999) pp. 2-8.*
Revilla et al. Comparison of Several Procedures Used for the Extraction of Anthocynains From Red Grapes; J. Agric. Food Chem. 1998, 46, pp. 4592-4597.7. 1q.*
Rumbold, T.F., MD: Hygenic and Sanative Measures for Chronic Catarrhal Inflammation; St. Louis, MO, Medical Journal Publishing Company, 1886, pp. 17-18.*
Steggall, J. MD: A Text Book of Materia Medica and Therapeutics; London, Oxford University Press, 1837, pp. 190-191.*
Wikipedia Online: Demulcent; Wikipedia Encyclopedia Online, URL<http://en.wikipedia.org/wiki/Demulcent>, one page.*
Nevins, J. B., MD: A Translation of the New London Pharmacopeia; Longman, Brown, Green and Longmans publishers; London, England, 1854, pp. 170-171.*
Plants for a Future Database; Online, URL<http://web.archive.org/web/20030414202519/http://www.ibiblio.org/pfaf/cgi-bin/arr_html?Malva+sylvestris&CAN=LATIND> archived to Apr. 2003 with Archive.org, Online <www.archive.org>, pp. 1-6.*
H. Eggensperger et al. : A Plant Extract With Potential; The Mucopolysaccharides of Malva Silvestris [sic] As Multi-Active Active Ingredients for Cosmetics; Parfumerie und Kosmetik; vol. 80, No. 7-8; 1999, pp. 10-12 (pp. 1-12 of full translation).*
John A. Wenninger, G.N. McEwen, Jr.,International Cosmetic Ingredient Dictionary and Handbook, (1997), 1626, 1650-1667,1673-1686, 1693-1697,Seventh Edition 1997, vol. 2, The Cosmetic, Toiletry, and Fragrance Association, Washington, DC.
M. Grieve, A Modern Herbal, The Medicinal, Culinary, Cosmetic and Economic Properties, Cultivation and Folk-Lore of Herbs,. Grasses, Fungi Shrubs & Trees with all their Modern Scientific Uses, vol. II, (I-Z and Indexes) 1981, pp. 779-781, Dover Publications, Inc. New York.

(Continued)

*Primary Examiner*—Patricia Leith

(57) ABSTRACT

The present invention relates to ingestible compositions containing *Cotinus coggygria* extract and/or *Malva sylvestris* extract and the use thereof in enhancing the elasticity or structural integrity of skin, urogenital tissue, blood vessel walls, or mucosal tissue and/or reducing the levels of triglycerides or uric acid.

9 Claims, No Drawings

OTHER PUBLICATIONS

J. Schmidgall et al., Evidence for Bioadhesive Effects of Polysaccharides and Polysaccharide-Containing Herbs in an ex vivo Bioadhesion Assay on Buccal Membranes, Planta Medica 66, 2000, pp. 48-53.

B. Classen et al., High Molecular Weight Acidic Polysaccharides from Malva sylvestris and Alcea rosea, Plant Medica 64, 1998, pp. 640-644.

N. G. Bisset et al., Herbal Drugs and Phytopharmaceuticals, Medpharm Scientific Publishers Stuttgart 1994, pp. 313-316.

K. C. Huang, The Pharmacology of Chinese Herbs, Second Edition, 1999, pp. 193-194, CRC Press.

T. Amadeu et al., Fibrillin-1 and Elastin are Differently Expressed in Hypertrophic Scars and Keloids, Wound Repair Regen, Mar.-Apr. 2004, vol. 12 No. 2 pp. 169-174.

Bhangoo KS, et al., Elastin Fibers in Scar Tissue., Plastic Reconstruction Surgeons, Oct. 1976, Mar. 1976 vol. 57No. 3 pp. 308-313.

T. Mizuno, et al., Overexpression of Elastin Fragments in Infarcted Myocardium Attenuates Scar Expansion and Heart Dysfunction, Am J Physiol Heart Circ Physiol. Jun. 2005;288(6): pp. H2819-H2827. Epub Jan. 28, 2005.

H. Westenburg, et al., Activity-Guided Isolation of Antioxidative Constituents of Cotinus Coggygria, Journal of Natural Products (2000), vol. 63, pp. 1696-1698.

B. Rousseau, et al., Characterization of Vocal Fold Scarring in a Canine Model, The Laryngoscope, vol. 113, Apr. 2003, pp. 620-627.

B. Rousseau et al., Characterization of Chronic Vocal Fold Scarring in a Rabbit Model, Journal of Voice, vol. 18,No. 1 (2004), pp. 116-124.

J. Laranne et al., Histological Changes in Elastic Components of Soft Palate Scars after $Co_2$ and Contact Nd:YAG Laser Incisions in the Dog as an Experimental Model, Eur Arch Otorhinolaryngol (1996), vol. 253, p. 454-459.

The New Royal Horticultural Society Dictionary of Gardening, Definition of Cotinus, 1999, pp. 739-740.

www.scs.leeds.ac.uk/cgi definition of Cotinus coggygria Sep. 23, 2004.

www.botanical.com definition of Sumachs Sep. 21, 2004.

www.bio-therapeutic.com Bio-Infusion contour Masque product order page Sep. 16, 2004.

www.outofthe forest.com IsaDermlx Phase Two Microdermabrasion product sheet Sep. 16, 2004.

www.bartleby.com, definition of sumac, Dec. 16, 2005.

www.homepeels.com, GlyMed Arnica Healing Cream order page, Dec. 15, 2005.

www.pharmabrands.com, AlphaDerma CE order page, Dec. 15, 2005.

Herbert J. Zeh III, et al., Addicted to Death, Invasive Cancer and the Immune Response to Unscheduled Cell Death, J Immunother, vol. 28, No. 1, Jan./Feb. 2005, pp. 1-9.

P Garcia-Lorda, et al., C-reactive protein, adiposity and cardiovascular risk factors in a Mediterranean population, International Journal of Obesity, 2005, pp. 1-7.

Samuel Klein, Outcome Success in Obesity, Obesity Research, vol. 9 Suppl., Nov. 4, 2001, pp. 354-358.

Arnold J. Altman, M.D., Uric Acid-Friend or Foe? Article.

James S. Forrester, M.D., Triglycerids: risk factor or fellow traveler?, Current opinion in Cardiology, 2001, 16:261-264.

www.nlm.nih.gov/medlineplus, Medline Plus Article, Medical Encyclopedia, Definition of Triglyeride Level.

Iris J.A.M. Jonkers, Hypertriglyceridemia Associated Risks and Effect of Drug Treatment, AM J. Cardiovasc Drugs 2001:1 (6) 455-466.

www.nlm.nih.gov/medlineplus, Medline Plus Article, Medical Encyclopedia, Definition of Uric Acid.

Mee-Shyuan Lee DrPh, et al., High prevalence of hyperuricemia in elderly Taiwanese, Asia Pac J. Clin Nutr 2005;14 (3); 285-292.

George J. Miller, Dietary fatty acids and the haemostatic system, Atherosclerosis 179 (2005) 213-227.

Joong Ho Bae, M.D., Acute Pancreatitis due to Hypertriglyceridemia: Report of 2 Cases, Korean J Gastroenterol 2005;46:475-480.

U.S. Appl. No. 11/313,079, filed Dec. 20, 2005, Johnson & Johnson Consumer Companies, Inc.

U.S. Appl. No. 11/248,465, filed Oct. 12, 2005, Johnson & Johnson Consumer Companies, Inc.

U.S. Appl. No. 11/973,313, filed Oct. 26, 2004, Johnson & Johnson Consumer Companies, Inc.

Emine Akalin, Kerim Alpinar, "An investigation on medicinal and edible wild plants of Tekirdag", *EGE Universitesi Eczalik Fakultesi Dergisi*, vol. 2, No. 1 (1994) pp. 1-11, English Abstract.

Kultur et al, "Medicinal plants used in Kirklareli Province (Turkey)", *Journal of Ethnopharmacology*, vol. 111, No. 2 (Dec. 12, 2006) pp. 341-364.

Tsankova et al, "Chemcial composition of the Bulgarian Sumac Oil", J. Essent. Oil Res., vol. 5 (1993) pp. 205-207(XP009087353).

Lucek RW, Colburn Wa, "Clinical pharmacokinetics of the retinoids", Clin Pharmacokinet., Jan.-Feb. 1985;10(1):38-62.

Tschan T, Steffen H, Supersaxo A., "Sebaceous-gland deposition of isotretinoin after topical application: an in vitro study using human facial skin", Skin Pharmacol. 1997;10(3):126-34.

Miyatake S, Ichiyama H, Kondo E, Yasuda K., "Randomized clinical comparisons of diclofenac concentration in the soft tissues and blood plasma between topical and oral applications", Br J Clin Pharmacol. Jan. 2009;67(1):125-9.

Pfau B, Kruse FE, Rohrschneider K, Zorn M, Fiehn W, Burk RO, Völcker HE., "Comparison between local and systemic administration of cyclosporine A on the effective level in conjunctiva, aqueous humor and serum", Ophthalmologe. Dec. 1995;92(6):833-9.

Demirci et al, "Composition of the Essential Oil of Cotinus Coggyria Scop. From Turkey", *Flavour and Fragrance Journal*, vol. 18, No. 1 (Jan. 2003) pp. 43-44.

Eggensperger et al, "Pflanzenextrakt Mit Potential Die Schleimpolysaccharide Von Malva Silvestris Als Multiaktive Wirkstoffe Fuer Kosmetika", Parfumerie und Kosmetik, Huethig, Heidelberg, DE, vol. 80, No. 7/8 (1999) pp. 10-12.

Guarrera et al, "Ethnobotanical and Ethnomedicinal Uses of Plants in the District of Acquapendente", Journal of Ethnopharmacology, vol. 96, No. 3 (Jan. 15, 2005), pp. 429-444.

Ivanova et al, "Polyphenols and Antioxidant Capacity of Bulgarian Medicinal Plants", *Journal of Ethnopharmacology*, vol. 96, No. 1-2, (Jan. 4, 2005) pp. 145-150.

Tsankova et al, "Chemical Composition of the Bulgarian Sumac Oil", *J. Essent.. Oil Res.*, vol. 5 (1993) pp. 205-207.

Wang Zhen-Yu, "Impact of Anthocyanin from Malva Sylvestris on Plasma Lipids and Free Radical", *Database Biosis [Online] Biosciences Information Service*, (Sep. 2005) Database accession No. PREV200600007804, Abstract only and *Journal of Forestry Research (Harbin)*, No. 16, No. 3 (Sep. 2005) pp. 228-232.

Herbal Blend Formulas; http://www.rgarden.com/products/masterblend.html, Mar. 23, 2006, one page.

Products Scan Online; Joey New York Intensive Collagen Boosting Treatment Patches—Chiseled Cheeks Contouring; Brow Lift; Double Chin Firminghffp://www.productsscan.com/search/fullrecord.cfm?frprt=302980, Mar. 23, 2006, one page.

Products Scan Online; Joey New York Intensive Collagen Boosting Treatment Patches—De-Puff and Eye bag Masque http://www.productsscan.com/search/fullrecord.cfm?frprt=302981, Mar. 23, 2006, one page.

Products Scan Online; Joey New York Intensive Collagen Boosting Treatment Patches—Lip Plumper http://www.productsscan.com/search/fullrecord.cfm?frprt=302982, Mar. 23, 2006, one page.

Products Scan Online; Colgate Herbal Propolis Fluoride Toothpaste—FreshMinthttp://www.productsscan.com/search/fullrecord.cfm?frprt=308764, Mar. 23, 2006, one page.

Mittendorf, W.F., MD: A Manual on Diseases of the Eye and Ear for the Use of Students and Practitioners; G.P. Putnam's Sons, New York, NY, 1881, p. 23.

Beasley, H., The Book of Presecriptions; J & A Churchill, London, England, 1883, p. 361.

Bedi et al. Herbal Therapy in Dermatology; Arch Dermatol. vol. 138, Feb. 2002, pp. 232-242.

Goodell, W. Am, MD: Lessons in Gynecology; F.A. Davis, Philadelphia, PA and New York, NY, 1891; pp. 482-483.

Steggall, J. MD: A Text Book of Materia Medica and Therapeutics; London, Oxford University Press, 1837, pp. 190-191.

Wikipedia Online: German Chamomile; Wikipedia Encylcopedia Online, URL <http://en.wikipedia.org/wiki/German_Chamomile>, accessed Nov. 15, 2007, pp. 1-2.

Wikipedia Online: Demulcent; Wikipedia Encyclopedia Online, URL <http://en.wikipedia.org/wiki/Demulcent>, accessed Nov. 1, 2007, one page.

Wikipedia Online: THYMOL; Wikipedia Encyclopedia Online, URL <http://en.wikipedia.org/wiki/Thymol>, accessed May 17, 2007, one page.

Drug Digests: Matricaria Chamomilla; URL <http://drugdigest.org/DD/DVH/HerbsWho/0;3923,4054%7Cmatricaria+chamomilla,00.html> accessed May 4, 2007, one page.

Stille, A. MD; Therapeutics and Materia Medica a Systematic Treatise of the Action and Uses of Medicinal Agents Including Their Description and History; Blanchard and ILea, Philadelphia, PA, 1860 pp. 127-128.

Wood, H.C. MD LLD; Therapeutics; Its Principles and Practice; J.B. Lipincott Company, London, England, 1892, pp. 758,760.

Parke, Davis & Company; Descriptive Catalogue of the Laboratory Products of Parke, Davis & Company; Parke, Davis & Company, Detroit, Michigan, 1894, p. 49.

'Fustic', The Dispensatory of the United States of America Twentieth Edition (1918), pp. 1, 65 and 66.

Henriette's plant info: Cotinus Coggygria Scop., Anacardiacea, accessed Feb. 7, 2007, one page, URL <http://www.henriettesherbal.com/php/get.php?id=12596>.

Ritter, T.J., "Mother's Remedies", G.H. Foote Publishing Company, p. 147, 1910.

Arbonne International, "Figure 8 Weight Loss Program", accessed May 20, 2008, one p., URL <http://www.gofigure8.com/pdf/supp.pdf.

* cited by examiner

INGESTIBLE COMPOSITIONS CONTAINING EXTRACTS

CROSS REFERENCE TO RELATED APPLICATIONS

This is a continuation-in-part of co-pending application Ser. No. 11/313,079, filed Dec. 20, 2005, which is a continuation-in-part of co-pending application Ser. No. 11/248,465, filed Oct. 12, 2005, which was a continuation-in-part of co-pending application Ser. No. 10/973,313, filed Oct. 26, 2004, which are hereby incorporated in their entirety.

BACKGROUND OF THE INVENTION

Aging of the skin is a complex phenomenon resulting from the interaction of several intrinsic and extrinsic factors. Intrinsic aging is an inevitable, genetically programmed process. Among extrinsic influences (e.g., wind, heat, cigarette smoke, chemicals, etc.), ultraviolet radiation appears to be the single most important factor associated with aging of the skin. The effect of ultraviolet radiation on elastic tissues results in elastosis, which is the accumulation of damaged elastin, resulting in reduced elasticity and resilience.

Elastin is a critical component of extracellular matrix, and is especially abundant in tissues subject to physical deformations, such as lungs, blood vessels and skin.

The effect of intrinsic aging on tissue elasticity of mucosal tissues (such as vaginal, oral, or rectal mucosal tissues) and of viscero-elastic tissues (that are lining body cavities such as the respiratory track, the gastrointestinal track, the urinal and bladder track, or the reproductive track) is very similar to the effect of intrinsic skin aging. Elastin fiber production in these tissues is reduced with aging, resulting in reduced responsiveness to stimuli. In the oral cavity, such changes can contribute to a decrease in the health of the gums (leading to reduced resistance to the pressure of food processing), increased gum bleeding, loose teeth, and a general decrease in the visual health parameters of the oral cavity. In the vagina, reduced elastin fiber production could result in stiffness and reduced sexual function, and uterine prolapse is associated with reduced elasticity of the female reproductive system. Reduced elasticity of the bladder can result in urine incontinence. Reduced elasticity of vessel walls can lead to vessel breakage and bruising. In the eye, degenerative changes in elastin fibers in Brunch's membrane can be responsible for deposition of drusen and macular degeneration.

Consequently, the reduction in elasticity of these tissues results in reduced quality of life and self esteem. Thus, it is desired to have a treatment that can prevent, retard, or reverse the intrinsic and extrinsic aging effects on tissue elasticity.

Triglycerides are a main constituent of vegetable oil and animal fats, and they play an important role in metabolism as energy sources. However, high triglyceride levels may be associated with a higher risk for atherosclerosis, heart disease, and stroke. (Forrester, J. S., Curr. Opin. Cardiology 2001, 16: 261-264). High triglyceride levels can also increase the risk of thrombosis, which can lead to myocardial infarction (Miller G. J., Atherosclerosis, 2005, 179:213-27). Hypertriglyceridemia is also a well known cause of acute pancreatitis, which can have life-threatening complications (Bae J. H. et al., Korean J Gastroenterol. 2005, 46:475-80). Current approaches for lowering triglycerides include diet and pharmacological agents, such as fibric acid derivatives, fish-oil, and CoA reductase inhibitors (Jonkers, I., et al., Am. J. Cardiovasc. Drugs 2001, 1:455-466).

Uric acid is an end product of purine metabolism. Purines are building blocks of RNA and DNA. Most uric acid produced in the body is excreted by the kidneys. An overproduction of uric acid occurs when there is excessive breakdown of cells, which contain purines, or an inability of the kidneys to excrete uric acid.

Hyperuricemia can play a role in the development of gout as well as many degenerative diseases, such as the Metabolic syndrome, which has been linked to a number of coronary heart diseases and increased mortality (Lee, M-Sh., et al., J. Clin. Nutr. 2005, 14:285:292). Hyperuricemia is also involved in the tumor lysis syndrome (TLS), which is a life-threatening constellation of metabolic derangements arising as a consequence of the release of intracellular metabolites by tumor cells as they undergo necrosis (Zeh, H J et al., J Immunother. 2005; 28:1-9). Uric acid and triglycerides were both found to be positively associated with C-reactive protein (CRP) levels (Garcia-Lorda P., et al., International Journal of Obesity (2005) 1-7).

Thus, it is desired to have a treatment that can prevent, retard, or reverse the negative cardiovascular effects induced by high blood levels of triglycerides and uric acid.

Malvaceae is a family of flowering plants that includes the mallows, cotton plants, okra plants, hibiscus, baobab trees, and balsa trees. The family traditionally consists of about 1,500 species in 75 genera. *Malva sylvestris* is a species from the *Malva* (mallow) genera. The leaves of *Malva sylvestris*, otherwise known as blue mallow, are rich in mucilage. The mucilage of *M. sylvestris* is made up of high molecular weight acidic polysaccharides (Classen B, et al., Planta Med 64(7): 640-44 (1988)). The leaf tea is traditionally believed to be useful as an anti-inflammatory, decongestant, humectant, expectorant, and laxative. It has also been used internally for soothing sore throats, laryngitis, tonsillitis, coughs, dryness of the lungs, and digestive upsets. Mallow is also used as a poultice for healing wounds and skin inflammations. In traditional medicine, mallow leaf tea is also used against abnormal growths of the stomach and to alleviate urinary infections (Bisset N G (ed). *Malvae folium*—Mallow leaf. In Herbal Drugs and Phyto-pharmaceuticals (1994, CRC Press, Stuttgart, pp 313-316). Studies on irritated mucus membranes have shown that the mucilage of *Malva sylvestris* binds to buccal membranes and other mucus membranes of the body (Schmidgall J, et al. Planta Med 66(1): 48-53(2000)).

*Cotinus coggygria* extract is traditionally believed to be useful as an anti-microbial treatment, used in the form of external washes. See, e.g., US Patent Applications Nos. 2002/0132021 where the extract is mentioned to be active against *E. coli, Staphylococcus aureus* and *S. cerevisiae*, as well as having anti-cancer activity. The dried leaf and twig of *Cotinus coggygria* is used in Chinese traditional medicine to eliminate "dampness" and "heat", and as an antipyretic (Huang K. C., *The Pharmacology of Chinese Herbs* (CRS Press, 1999, pp 193-194). A yellow/orange dye can be obtained from the root and stem and can be used for fabric dying. The leaves and bark are a good source of tannins (Grieve M. A Modern Herbal. Dover Publications, Inc. NY, 1971, pp 779-781).

The present invention relates to the unexpected discovery that *Malva sylvestris* and *Cotinus coggygria* extracts, when ingested, are both effective for enhancing the elasticity of the skin, urogenital, blood vessel walls, and mucosal tissues, as well as reducing triglyceride and uric acid levels.

SUMMARY OF THE INVENTION

In one aspect, the present invention features an ingestible composition containing *cotinus coggygria* extract and *malva sylvestris* extract.

In another aspect, the present invention features a method of enhancing the elasticity or structural integrity of skin, blood vessel walls, urogenital tissue, or mucosal tissue of a mammal in need of such enhancement by the ingestion by such mammal of a composition containing an extract of *cotinus coggygria, malva sylvestris* or mixtures thereof.

In another aspect, the present invention features a method of reducing the levels of triglycerides or uric acid in a mammal in need of such reduction by the ingestion by such mammal of a composition containing an extract of *cotinus coggygria, malva sylvestris*, or mixtures thereof.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage refers to a percentage by weight (i.e., % (W/W)).

DEFINITIONS

What is meant by "enhancing the elasticity or structural integrity" is increasing, preventing the loss, or retarding the loss of elasticity or structural integrity of the tissue, including but not limited to, treating sagging, lax and loose tissues and tightening and strengthening tissues, such as skin, mucosal tissues, urogenital tissues, and blood vessels.

The loss of elasticity or tissue structure integrity may be a result of a number of factors, including but not limited to disease, aging, hormonal changes, mechanical trauma, environmental damage, or the result of an application of products, such as a cosmetics or pharmaceuticals, to the tissue.

What is meant by "reducing triglyceride or uric acid" is, respectively, reducing the level, or preventing the increase in the level, of triglycerides ("TG") in serum or of uric acid ("UA") in the serum and/or urine.

The increase in triglyceride or uric acid levels in the body may be a result of a number of factors, including but not limited to disease, aging, hormonal changes, environmental damage, genetic factors, nutritional imbalance, and the like.

What is meant by "mucosal tissues" are tissues that express elastin and are composed in part of cells of mesenchymal and epithelial origin. Examples of mucosal tissues include, but are not limited to, vaginal, oral, corneal, nasal, rectal, and viscero-elastic tissues. Examples of viscero-elastic tissues are those that line the respiratory track, blood vessel walls, the gastro-intestinal track, the urinary track, the bladder, and the reproductive track.

What is meant by "urogenital tissues" are tissues of the bladder, the urinary track, and the reproductive track, including but not limited to the vagina, clitoris, external genitalia, uterus, bladder, and urethra.

What is meant by "vessel walls" are walls of vessels of the circulatory system that function to transport blood or lymph throughout the body, including, but not limited to, arteries and veins.

What is meant by a "product" is a product in finished packaged form. In one embodiment, the package is a container such as a plastic, metal or glass bottle or jar containing the composition or a "blister pack" for containing unit dosages of the composition. The product may further contain additional packaging such as a plastic or cardboard box for storing such container. In one embodiment, the product contains instructions directing the user to ingest the composition (e.g., for the purposes set forth herein). Such instructions may be printed on the container, label insert, or on any additional packaging.

What is meant by "promoting" is promoting, advertising, or marketing. Examples of promoting include, but are not limited to, written, visual, or verbal statements made on the product or in stores, magazines, newspaper, radio, television, internet, and the like. Examples of such statements include, but are not limited to, "enhances skin elasticity or structural integrity," "improving visible and tactilely perceptible manifestations of the skin," "increases skin elasticity or structure," "restores skin elasticity or structure," "treats sagging of lax skin," "enhances vaginal elasticity," "enhances sexual satisfaction," "increases vaginal elasticity," "restores vaginal elasticity," "strengthen vaginal wall," "prevents or treats vaginal prolapse," "reduces incontinence episodes," "strengthen bladder wall," "improves bladder compliance," "enhances gum elasticity," "increases gum elasticity," "restores gum elasticity," "enhances alveolar wall elasticity," "increases alveolar wall elasticity," "enhances the healthy look of the gums," "restores alveolar wall elasticity," "decreases the risk of cardiovascular diseases," "decreases the risk of pancreatitis," "reduces pancreatitis," "decreases the risk of thrombosis," "reduces thrombosis," "lowers C-reactive protein (CRP)," "decreases systolic and diastolic blood pressure," "lowers tissue edema," "reduces gout," "reduces tumor lysis syndrome," "slows or reverses age-related metabolic syndromes," "slows or reverses disease-related metabolic syndromes," "enhances vessel wall strength," "improves fragile skin," "decreases bruising," and "decreases inflammatory cell extravasation."

As used herein, "ingestible composition" means a composition that is intended to be ingested. Examples of forms of ingestible compositions include, but are not limited to, tablets, pills, capsules, powders, granules, solutions or suspensions, and drops. Ingestible compositions do not include compositions intended to be topically administered to the skin or oral, vaginal, or rectal cavity.

As used herein, "pharmaceutically-acceptable" means that the ingredients which the term describes are suitable for ingesting without undue toxicity, incompatibility, instability, irritation, allergic response, and the like.

As used herein, "safe and effective amount" means an amount of the extract or of the composition sufficient to induce the desired effect, but low enough to avoid serious side effects. The safe and effective amount of the compound, extract, or composition will vary with e.g. the age, health and environmental exposure of the end user, the duration and nature of the treatment, the specific extract, ingredient, or composition employed, the particular pharmaceutically-acceptable carrier utilized, and like factors.

*Malva Sylvestris* Extract

What is meant by a "*Malva sylvestris* extract" is a blend of compounds isolated from the plant *Malva sylvestris*. In one embodiment, the compounds are isolated from the flowers of the plant. In a further embodiment, the compounds are isolated from dried flowers of the plant. Such compounds may be isolated from one or more part of the plant (e.g., the whole plant, flower, seed, root, rhizome, stem, fruit and/or leaf of the plant) by physically removing a piece of such plant, such as grinding a flower of the plant. Such compounds may also be isolated from the plant by using extraction procedures well known in the art (e.g., the use of organic solvents such as lower $C_1$-$C_8$ alcohols, $C_1$-$C_8$ alkyl polyols, $C_1$-$C_8$ alkyl ketones, $C_1$-$C_8$ alkyl ethers, acetic acid $C_1$-$C_8$ alkyl esters, and chloroform, and/or inorganic solvents such as water, inorganic acids such as hydrochloric acid, and inorganic bases such as sodium hydroxide). In one embodiment, the *Malva sylvestris* extract contains only hydrophilic compounds (e.g., isolated by using a hydrophilic solvent, such as water or ethanol). In one embodiment, the *Malva sylvestris* extract is an aqueous extract from the flowers. In one embodiment, the *Malva sylvestris* extract is an aqueous extract from the flowers of *Malva sylvestris* that is subsequently dried to a powder, which optionally is later reconstituted to the desired concentration in the final composition and is optionally filtered.

In one embodiment, the extract is present in a composition (e.g., in a pill) taken in an amount from about 0.5 to about 500 mg, in particular in an amount from about 10 to about 250 mg by weight. Unless stated otherwise, the weight of the extract refers to the dry weight of the extract.

*Cotinus Coggygria* Extract

What is meant by a "*Cotinus coggygria* extract" is a blend of compounds isolated from a *Cotinus coggygria* plant. In one embodiment, the compounds are isolated from the leaf of the plant. In a further embodiment, the compounds are isolated from dried leaves of the plant. Such compounds may be isolated from one or more parts of the plant (e.g., the whole plant, flower, seed, root, rhizome, bark, wood, stem, fruit and/or leaf of the plant) by physically removing a piece of such plant, such as grinding a root of the plant. Such compounds may also be isolated from the plant by using extraction procedures well known in the art (e.g., the use of organic solvents such as lower $C_1$-$C_8$ alcohols, $C_1$-$C_8$ alkyl polyols, $C_1$-$C_8$ alkyl ketones, $C_1$-$C_8$ alkyl ethers, acetic acid $C_1$-$C_8$ alkyl esters, and chloroform, and/or inorganic solvents such as water, inorganic acids such as hydrochloric acid, and inorganic bases such as sodium hydroxide). In one embodiment, the *Cotinus coggygria* extract contains only hydrophilic compounds (e.g., isolated by using a hydrophilic solvent, such as water or ethanol). In one embodiment, the *Cotinus coggygria* extract is an aqueous extract from the leaf of *Cotinus coggygria*. In one embodiment, the *Cotinus coggygria* extract is an aqueous extract from the leaf of *Cotinus coggygria* that is subsequently dried to a powder, which optionally is later reconstituted to the desired concentration in the final composition and is optionally filtered.

In one embodiment, the extract is present in a composition (e.g., in a pill) taken in an amount from about 0.5 to about 500 mg, in particular in an amount from about 10 to about 250 mg by weight. Unless stated otherwise, the weight of the extract refers to the dry weight of the extract.

Other Extracts

In one embodiment, the compositions of the present invention contain one or more of the extracts from plants selected from the group consisting of *Matricaria chamomilla, Thymus vulgaris, Thymus serpyllum, Arctostaphyllos uva-ursi,* and *Matricaria recutita*. In one embodiment, the extract is present in a composition (e.g., in a pill) taken in an amount from about 0.5 to about 500 mg, in particular in an amount from about 10 to about 250 mg by weight. Unless stated otherwise, the weight of the extract refers to the dry weight of the extract.

Ingestible Compositions

The ingestible compositions useful in the present invention involve formulations suitable for ingesting by the mammal, such as a human, in need to such treatment. In one embodiment, the compositions contain a safe and effective amount of (i) *Malva sylvestris* extract and/or *Cotinus coggygria* extract and (ii) a pharmaceutically-acceptable carrier.

In one embodiment, the ingestible compositions herein contain, per dosage unit, e.g., tablet, capsule, powder, injection, teaspoonful and the like, an amount of the extract(s) necessary to deliver an effective dose as described above. In one embodiment, the ingestible compositions herein contains, per unit dosage unit, e.g., tablet, capsule, powder, teaspoonful and the like, of from about 1 mg to about 5 g, such as from about 50 mg to about 500 mg, and may be given at a dosage of from about 1 mg/kg/day to about 1 g/kg/day, such as from about 50 to about 500 mg/kg/day. The dosages, however, may be varied depending upon the requirement of the patients, the severity of the condition being treated, and the extract(s) being employed. The use of either daily administration or post-periodic dosing may be employed. Preferably these compositions are in unit dosage forms from such as tablets, pills, capsules, powders, granules, solutions or suspensions, and drops.

In one embodiment, the compositions are provided in the form of tablets, such as those containing 1, 5, 10, 25, 50, 100, 150, 200, 250, 500, and/or 1000 milligrams of the extract(s) for the symptomatic adjustment of the dosage to the patient to be treated. The extract(s) may be administered on a regimen of 1 to 4 times per day. Advantageously, the compositions may be administered in a single daily dose, or the total daily dosage may be administered in divided doses of two, three or four times daily.

Optimal dosages to be administered may be readily determined by those skilled in the art, and will vary with the particular extract(s) used, the mode of administration, the strength of the preparation, and the advancement of the disease/condition being treated. In addition, factors associated with the particular patient being treated, including patient age, weight, diet and time of administration, will result in the need to adjust dosages.

Ingestible compositions containing one or more of the extracts of the invention described herein can be prepared by intimately mixing the extract(s) with a pharmaceutically-acceptable carrier according to conventional pharmaceutical compounding techniques. The carrier may take a wide variety of forms depending upon the type of formulation. Thus for liquid preparations such as suspensions, elixirs and solutions, suitable carriers and additives include but not limited to water, glycols, alcohols, flavoring agents, preservatives, stabilizers, coloring agents and the like; and for solid preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption.

For preparing solid compositions such as tablets, the principal extract(s) is mixed with a pharmaceutically-acceptable carrier, e.g. conventional tableting ingredients such as corn starch, lactose, sucrose, sorbitol, talc, stearic acid, magnesium stearate, dicalcium phosphate or gums, and other pharmaceutically-acceptable diluents, e.g. water, to form a solid preformulation composition containing a homogeneous mixture of the extract(s). When referring to these preformulation compositions as homogeneous, it is meant that the extract(s) is dispersed evenly throughout the composition so that the composition may be readily subdivided into equally effective dosage forms such as tablets, pills and capsules. This solid preformulation composition may then subdivided into unit dosage forms of the type described above. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention include but not limited to aqueous and/or organic (e.g., ethanol) solutions, suitably flavoured syrups, aqueous suspensions, and flavoured emulsions as well as elixirs and similar pharmaceutically-acceptable vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

In one embodiment, the compositions further contain nutritional ingredients. Such nutritional ingredients may be in the form of botanical extracts, natural and synthetic molecules, minerals, and/or mixtures thereof.

Examples of nutritional ingredients include, but are not limited to proteins, vitamins (such as retinoids and various form of tocopherol), minerals (such as zinc, iron or selenium), anti-oxidants (such as ascorbates, lycopenes, or carotenes), proteins, peptides, fatty acids (such as omega-3 fatty acids), extracts of pomegranate and green tea, and phenolic compounds such as resveratrol.

One skilled in the art will recognize that, both in vivo and in vitro trials using suitable, known and generally accepted cell and/or animal models are predictive of the ability of an extract to treat or prevent a given condition. One skilled in the art will further recognize that human clinical trails including first-in-human, dose ranging and efficacy trials, in healthy patients and/or those suffering from a given condition or disorder, may be completed according to methods well known in the clinical and medical arts.

EXAMPLE 1

Extract Preparations

The following is a description of the preparation of various extracts of the present invention. As used in the subsequent Examples, the weight percentage of extract refers to the weight of the liquid extract.

A: *Malva Sylvestris* Extract Preparation.

*Malva sylvestris* (whole dried flowers) was purchased from Botanic Choice (Hobart, Ind.) or Bilek (Troyan, Bulgaria). Ten grams of whole flowers were placed in 200 ml cold water, and brought to boiling in a sealed container. After the appearance of the boiling bubbles, the container was immediately withdrawn from the heating source, covered, and stored at room temperature for from about 1 hour to about 12 hours, with occasional agitation. The extract was then filtered through gauze, and excess liquid was squeezed manually from herbs to maximize the extract yield. The extract was either used as is or was further filtered through 22-micrometer 250 ml filtering unit from Nalgene (Rochester, N.Y.), under vacuum.

Alternatively, *Malva sylvestris* extract was prepared by adding ten grams of whole flowers to 200 ml cold water, and agitating the mixture at room temperature for from about 1 hour to about 12 hours. The extract was then filtered as described above.

Alternatively, *Malva sylvestris* extract was prepared by adding ten grams of whole flowers to 200 ml cold water, and then boiling the mixture in a sealed container. After the appearance of boiling, the container was withdrawn from the heating source, covered, and stored at room temperature for from about 1 hour to about 12 hours. After such time, ethanol was added to the extract to a final concentration of about 45%, volume of the total mixture. The extraction was continued at room temperature for additional 1 to 12 hours, with agitation. The extract was either used as is or was filtered as described above.

Alternatively, *Malva sylvestris* extract was prepared as described above and dried. The evaporation was completed under helium lamp with a drying temperature of 100° C. The resulting dried powder was then resuspended to the original concentration with water ("*Malva sylvestris* reconstituted"). Filtration was performed by passing the liquid through a 0.22 micrometer filter (Nalgene, Rochester, N.Y.). Using a HR73 Moisture Analyzer (Mettler-Toledo, Columbus, Ohio) to quantify the evaporating moisture at 30-second intervals, the dry content in the extracts prepared as described above was determined to be approximately 1.40% solids.

B: *Cotinus Coggygria* Extract Preparation.

*Cotinus coggygria* herb (whole dried leaf) was purchased from Bilkokoop (Sofia, Bulgaria). Ten grams of whole leaves were placed in 100 ml cold water, and brought to boiling in a sealed container, and boiled for 5 minutes. The container was then immediately withdrawn from the heating source, covered, and stored at room temperature for from about 1 hour to about 12 hours, with occasional agitation. After this, the extract was filtered through gauze, and excess liquid was squeezed manually from herbs to maximize the extract yield. The extract was either used as is or was further filtered through 22-micrometer 250 ml filtering unit from Nalgene (Rochester, N.Y.), under vacuum.

Alternatively, *Cotinus coggygria* extract was prepared by drying the extracts prepared as described above. The evaporation was completed under helium lamp with a drying temperature of 100° C. The resulting dried powder was then resuspended to the original concentration with water ("*Cotinus coggygria* reconstituted"). Filtration was performed by passing the liquid through a 0.22 micrometer filter (Nalgene, Rochester, N.Y.). Using a HR73 Moisture Analyzer (Mettler-Toledo, Columbus, Ohio) to quantify the evaporating moisture at 30-second intervals, the dry content in the extracts prepared as described above was determined to be approximately 2.39% solids.

C: *Matricaria Chamomilla* Extract Preparation

*Matricaria chamomilla* herb (whole dried flowers) was purchased from Bilek (Troyan, Bulgaria). *Matricaria recutita* herb (whole dried flowers) was purchased from Botanic Choice (Hobart, Ind.). Ten grams of whole flowers were placed in 200 ml cold water, and brought to boiling in a sealed container. After the appearance of the boiling bubbles, the container was immediately withdrawn from the heating source, covered, and stored at room temperature for from about 1 hour to about 12 hours, with occasional agitation. After this, the extract was filtered through gauze, and excess liquid was squeezed manually from herbs to maximize the extract yield. The extract was either used as is or was further filtered through 22-micrometer 250 ml filtering unit from Nalgene (Rochester, N.Y.), under vacuum.

Alternatively, *Matricaria chamomilla* extract was prepared by drying the extracts prepared as described above. The evaporation was completed under helium lamp with a drying temperature of 100° C. The resulting dried powder was then resuspended to the original concentration with water ("*Matricaria chamomilla* reconstituted"). Filtration was performed by passing the liquid through a 0.22 micrometer filter (Nalgene, Rochester, N.Y.). Using a HR73 Moisture Analyzer (Mettler-Toledo, Columbus, Ohio) to quantify the evaporating moisture at 30-second intervals, the dry content in the extracts prepared as described above was determined to be approximately 2.07% solids.

D: *Arctostaphylos uva-ursi* Extract Preparation.

*Arctostaphylos uva-ursi* herb (whole dried leaf) was purchased from Bilkokoop (Sofia, Bulgaria). Ten grams of whole leaves were placed in 100 ml cold water, and brought to boiling in a sealed container, and boiled for 5 minutes. The container was then immediately withdrawn from the heating source, covered, and stored at room temperature for from about 1 hour to about 12 hours, with occasional agitation. After this, the extract was filtered through gauze, and excess liquid was squeezed manually from herbs to maximize the extract yield. The extract was either used as is or was further filtered through 22-micrometer 250 ml filtering unit from Nalgene (Rochester, N.Y.), under vacuum.

Alternatively, *Arctostaphylos uva-ursi* extract was prepared by drying the extracts prepared as described above. The evaporation was completed under helium lamp with a drying temperature of 100° C. The resulting dried powder was then resuspended to the original concentration with water ("*Arctostaphylos uva-ursi* reconstituted"). Filtration was performed by passing the liquid through a 0.22 micrometer filter (Nalgene, Rochester, N.Y.). Using a HR73 Moisture Analyzer (Mettler-Toledo, Columbus, Ohio) to quantify the evaporating moisture at 30-second intervals, the dry content in the extracts prepared as described above was determined to be approximately 3.08% solids.

E: *Thymus serpyllum* Extract Preparation.

*Thymus serpyllum* herb (dried stem) was purchased from Bilek (Troyan, Bulgaria). Ten grams of whole herb were placed in 200 ml cold water, and brought to boiling in a sealed container. After the appearance of the boiling bubbles, the container was immediately withdrawn from the heating source, covered, and stored at room temperature for from about 1 hour to about 12 hours, with occasional agitation. The extract was then filtered through gauze, and excess liquid was squeezed manually from herbs to maximize the extract yield. The extract was either used as is or was further filtered through 22-micrometer 250 ml filtering unit from Nalgene (Rochester, N.Y.), under vacuum.

Alternatively, *Thymus serpyllum* extract was prepared by drying the extracts prepared as described above. The evaporation was completed under helium lamp with a drying temperature of 100° C. The resulting dried powder was then resuspended to the original concentration with water ("*Thymus serpyllum* reconstituted"). Filtration was performed by passing the liquid through a 0.22 micrometer filter (Nalgene, Rochester, N.Y.). Using a HR73 Moisture Analyzer (Mettler-Toledo, Columbus, Ohio) to quantify the evaporating moisture at 30-second intervals, the dry content in the extracts prepared as described above was determined to be approximately 2.38% solids.

F: Herbal Combination Extract Preparation

*Malva sylvestris* herb (whole dried flowers) was purchased from both Bilek (Troyan, Bulgaria) or Botanic Choice (Hobart, Ind.). *Matricaria chamomilla* herb (whole dried flowers) was purchased from Bilek (Troyan, Bulgaria). *Matricaria recutita* was purchased from Botanic Choice (Hobart, Ind.). *Thymus serpyllum* herb (dried stem) was purchased from Bilek (Troyan, Bulgaria). *Cotinus coggygria* herb (whole dried leaf) was purchased from Bilkokoop (Sofia, Bulgaria). *Thymus vulgaris* herb (dried stem) was purchased from Starwest Botanicals (Rancho Cordova, Calif.). Amounts of herbs, as described in Tables 1, 2, and 3 below, were placed together in 250 ml cold water and brought to boiling in a sealed container. After the appearance of the boiling bubbles, the container was immediately withdrawn from the heating source, covered, and stored at room temperature for from about 1 hour to about 12 hours with occasional agitation. The extract was then filtered through gauze, and excess liquid was squeezed manually from herbs to maximize the extract yield. The extract was used as is or was further filtered through 22-micrometer 250 ml filtering unit from Nalgene (Rochester, N.Y.), under vacuum.

Using a HR73 Moisture Analyzer (Mettler-Toledo, Columbus, Ohio) to quantify the evaporating moisture at 30 second intervals, the dry content in the extracts prepared as described above, was determined to be approximately 2% solids.

TABLE 1

| Name | Amount |
| --- | --- |
| *Malva sylvestris* L. | 4 g |
| *Thymus serpyllum* | 7 g |
| *Matricaria chamomilla* L. | 7 g |
| Water | 250 ml |

TABLE 2

| Name | Amount |
| --- | --- |
| *Malva sylvestris* L. | 4 g |
| *Thymus vulgaris* | 7 g |
| *Matricaria recutita* L. | 7 g |
| Water | 250 ml |

TABLE 3

| Name | Amount |
| --- | --- |
| *Malva sylvestris* L. | 4 g |
| *Cotinus coggygria* | 2.2 g |
| *Matricaria chamomilla* L. | 7 g |
| Water | 250 ml |

Alternatively, the individual extracts of the herbs were separately made (e.g., as described in Examples 1A-1E) and subsequently combined together at a desired proportion ("Extract combined").

EXAMPLE 2

Enhancement of Elastin Promoter Activity

Rat cardiac myoblasts H9C2 were purchased from ATCC (Manassas, Va.). Cultures were maintained in Dulbecco's modified Eagle's medium (DMEM, Invitrogen Life Technologies, Carlsbad, Calif.) supplemented with 10% fetal bovine serum, 2 mM glutamine, 100 units/ml penicillin, and 50 µg/ml streptomycin (Invitrogen life technologies, Carlsbad, Calif.).

Cell cultures were transiently transfected with the elastin promoter-luciferase reporter construct (Elp2.2, a 2.2 kb elastin promoter fragment from nt−2267 to nt+2, driving the firefly luciferase gene, which was obtained from Promega, Madison Wis.). DNA was prepared by Qiagen Maxi columns (Qiagen Valencia, Calif.). In all transfections, a construct with the thymidine kinase promoter and the *Renilla* luciferase reporter gene (pRL-TK, Promega, Madison Wis.) was included as an internal control. Cells were plated at $4\times10^4$ in each well of a 24-well plate (Corning Incorporated, Corning, N.Y.) in growth media without antibiotics for 24 hours, reaching 80-90% confluency at the time of transfection. Typically, cells were transfected with 0.8 μg DNA per well using Lipofectamine 2000 (Invitrogen life technologies, Carlsbad, Calif.). One day after transfection, cells were treated with agents at indicated concentrations for approximately 48 hours before they were lysed for luciferase assays, using Dual-Luciferase Reporter System from Promega (Madison, Wis.), following manufacture's protocol. Briefly, the firefly luciferase activity was measured first (representing elastin promoter activity), followed by the *renilla* luciferase (internal control), using luminometer LMAX, from Molecular Devices (Sunnyvale, Calif.). The ratio of these two luciferase activities (RLU) was used to evaluate the activity of each promoter.

Cells were treated with various doses of *Malva Sylvestris* extract (Example 1A), *Coggygria* extract (Example 1B), *Matricaria chamomilla* extract (Example 1C), *Arctostaphylos uva-ursi* extract (Example 1D), *M. sylvestris/M. chamomilla/Thymus serpyllum* extract (Example 1F), *M. sylvestris/M. chamomilla/cotinus coggygria* (Example 1F) or *M. sylvestris/M. recutita/Thymus vulgaris* extract (Example 1F) and the effect of the extract on the induction of expression from the elastin promoter was evaluated. The extracts were added to the transfected H9C2 cells and were incubated for 48 hours. An increase in elastin promoter activity was observed in the presence of increasing doses of the extracts, as compared to untreated cells, as shown in Table 4. This example demonstrates that each of the extracts, alone or in combination, could enhance elastin production.

TABLE 4

| Agent (% W/W) | Induction |
|---|---|
| Control - no extract added | 1 +/− 0 |
| *Malva sylvestris* (2.5%) | 1.93 +/− 0.33 |
| *Malva sylvestris* (5%) | 2.27 +/− 0.03 |
| *Malva sylvestris* reconstituted(2.5%) | 1.1 +/− 0.12 |
| *Cotinus coggygria* (0.05%) | 1.56 +/− 0.34 |
| *Cotinus coggygria* (0.1%) | 1.52 +/− 0.18 |
| *Cotinus coggygria* (0.15%) | 1.5 +/− 0 |
| *Cotinus coggygria* reconstituted(0.05%) | 1.1 +/− 0.03 |
| *Matricaria chamomilla* (5%) | 1.65 +/− 0.25 |
| *Arctostaphylos uva-ursi* (2.5%) | 1.56 +/− 0.34 |
| *Malva sylvestris* (5%) and *Cotinus coggygria* (0.1%) | 2.7 +/− 0 |
| *Malva sylvestris* (2.5%) and *Arctostaphylos uva-ursi* (2.5%) | 2.9 +/− 0.56 |
| *Cotinus coggygria* (0.05%)and *Arctostaphylos uva-ursi* (2.5%) | 2.27 +/− 0 |
| *Malva sylvestris/Matricaria recutita/Thymus vulgaris* (2%) | 1.66 +/− 0 |
| *Malva sylvestris/Matricaria chamomilla/Thymus serpyllum* (2%) | 2.2 +/− 0 |
| *Malva sylvestris/Matricaria chamomilla/Thymus Vulgaris* (2%) and *Cotinus coggygria* (0.15%) | 3.3 +/− 0 |
| *Malva sylvestris/Matricaria chamomilla/Cotinus coggygria* (2.5%) | 1.4 +/− 0.1 |
| *Malva sylvestris/Matricaria chamomilla/Cotinus coggygria* reconstituted(2.5%) | 1.1 +/− 0.2 |
| *Malva sylvestris* (0.77%) and *Matricaria chamomilla* (1.35%) and *Cotinus coggygria* (0.38%) combined | 2.38 +/− 0.36 |
| *Malva sylvestris* (1.54%) and *Matricaria chamomilla* (2.7%) and *Cotinus coggygria* (0.76%) combined | 3.39 +/− 0.14 |

EXAMPLE 3

Protection from Elastase Degradation

Human leukocyte elastase (HLE) was purchased from Sigma (St. Louis, Mo.), and reconstituted at 1 unit/ml in phosphate buffered saline (PBS, Invitrogen life Technologies, Carlsbad, Calif.). Soluble bovine neck ligament elastin labeled with BODIPY FL dye was purchased from Molecular Probes, Inc. (Eugene, Oreg.), such that the fluorescence was quenched in the conjugate, and could be activated upon elastase digestion. Human leukocyte elastase (0.0625 U/ml), elastin substrate (25 μg/ml), and increasing concentrations of test material were incubated for one hour at room temperature. Fluorescence was measured at excitation at 490 nm and emission at 520 nm using a fluorescent plate reader Gemini from Molecular Devices (Sunnyvale, Calif.). Background fluorescence of substrate alone had been subtracted from each measurement.

Two batches of *Cotinus coggygria* extracts, prepared according to Example 1B, were averaged in the experiment, with data presented as compared to controls with no extract added. *Cotinus coggygria* extracts inhibited HLE activity in a dose dependent manner as shown in Table 5. As low as 0.01% of *Cotinus coggygria* extract resulted in approximately 60% reduction in HLE activity, while 0.1% of extract almost completely inhibited elastase activity. This example demonstrates that *Cotinus* extract can protect elastin fibers from damage and degradation.

TABLE 5

| *Cotinus* Extract (% W/W) | Elastase Inhibition (%) |
|---|---|
| 0 | 0 +/− 1.6 |
| 0.0001 | 2.8 +/− 1.2 |
| 0.001 | 15.35 +/− 5.85 |
| 0.01 | 50 +/− 15 |
| 0.1 | 97.6 +/− 0 |

The HLE activity of the reconstituted *Cotinus* extract of Example 1B was also assessed (Table 6). Reconstituted *Cotinus coggygria* extract inhibited HLE activity in a dose dependent manner, with activities similar to the original *Cotinus* extract (Table 5).

TABLE 6

| *Cotinus* Extract reconstituted(% W/W) | Elastase Inhibition (%) |
|---|---|
| 0 | 0 |
| 0.0125 | 23.37 |
| 0.025 | 42.21 |
| 0.05 | 68.54 |
| 0.1 | 83.11 |

EXAMPLE 4

Protection from Trypsin Degradation

Trypsin was purchased from Sigma (St. Louis, Mo.), and reconstituted at 2000 unit/ml in phosphate buffered saline (PBS, Invitrogen life technologies, Carlsbad, Calif.). Casein labeled with BODIPY FL dye was purchased from Molecular Probes, Inc., (Eugene, Oreg.), such that the fluorescence was quenched in the conjugate, and could be activated upon protease digestion. Trypsin (500 U/ml), Casein (10 μg/ml), and increasing concentrations of test agent, were incubated for two hours at room temperature. Fluorescence was measured at excitation at 485 nm and emission at 538 nm using a fluorescent plate reader Gemini from Molecular Devices (Sunnyvale, Calif.). Background fluorescence of substrate alone had been subtracted from each measurement.

Two batches of *Cotinus coggygria* extracts, prepared as described in Example 1B, were averaged in the experiment, with data presented as compared to controls with no extract added. *Cotinus coggygria* extract inhibited trypsin activity in a dose dependent manner as shown in Table 7. As low as 0.02% of *Cotinus coggygria* extract resulted in approximately 35% reduction in trypsin activity, while addition of 0.1% of extract resulted in approximately 61% inhibition of trypsin activity. This example demonstrates that *Cotinus* extract can protect tissues from proteolytic damage and degradation, therefore maintaining tissue integrity.

TABLE 7

| *Cotinus* Extract (% W/W) | Trypsin Inhibition (%) |
|---|---|
| 0 | 0 +/− 0 |
| 0.008 | 0 +/− 0 |
| 0.004 | 6.4 +/− 6.4 |
| 0.02 | 34.6 +/− 14.9 |
| 0.1 | 60.9 +/− 6.2 |

EXAMPLE 5

Protection from Matrix Metalloproteinase Degradation

Human macrophage elastase (HME, also named Matrix Metalloproteinase-12, MMP-12) and fluorescently labeled substrate were purchased from R&D systems (Minneapolis, Minn.). The fluorescence was quenched in the substrate, and could be activated upon elastase digestion. HME (100 ng/ml), substrate (10 μg/ml), and increasing concentrations of test material were incubated for one hour at room temperature. Fluorescence was measured at excitation at 320 nm and emission at 405 nm using a fluorescent plate reader Gemini from Molecular Devices (Sunnyvale, Calif.). Background fluorescence of substrate alone had been subtracted from each measurement.

Two batches of *Cotinus coggygria* extracts, prepared according to Example 1B, were averaged in the experiment, with data presented as compared to controls with no extract added. *Cotinus coggygria* extracts inhibited HME activity in a dose dependent manner as shown in Table 8. As low as 0.01% of *Cotinus coggygria* extract resulted in approximately 40% reduction in HME activity, while 0.5% of extract almost completely inhibited HME activity. This example demonstrates that *Cotinus* extract can protect elastin fibers from damage and degradation.

TABLE 8

| *Cotinus* Extract (% W/W) | HME Inhibition (%) |
|---|---|
| 0 | 0 |
| 0.01 | 37.6 +/− 2.4 |
| 0.05 | 69.6 +/− 1.0 |
| 0.1 | 79.5 +/− 1.5 |
| 0.5 | 96.3 +/− 0.4 |

*Malva* extracts, prepared according to Example 1A, were tested in the same experiment, with data presented as compared to controls with no extract added. *Malva* extract inhibited HME activity in a dose dependent manner as shown in Table 9. As low as 0.6% of *Malva* extract resulted in approximately 23% reduction in HME activity, while 5% of extract inhibited HME activity 80%. This example demonstrates that *Malva* extract can protect elastin fibers from damage and degradation.

TABLE 9

| *Malva* Extract (% W/W) | HME Inhibition (%) |
|---|---|
| 0 | 0 |
| 0.6 | 22.0 +/− 0.9 |
| 1.25 | 40.1 +/− 0.0 |
| 2.5 | 62.0 +/− 0.6 |
| 5 | 79.3 +/− 1.2 |

*Arctostaphylos uva-ursi* extracts, prepared according to Example 1D, were tested in the same experiment, with data presented as compared to controls with no extract added. *Arctostaphylos uva-ursi* extract inhibited HME activity in a dose dependent manner as shown in Table 10. As low as 0.01% of *Arctostaphylos uva-ursi* extract resulted in approximately 10% reduction in HME activity, while 0.5% of extract inhibited HME activity 90%. This example demonstrates that *Arctostaphylos uva-ursi* extract can protect elastin fibers from damage and degradation.

TABLE 10

| *Arctostaphylos uva-ursi* Extract (% W/W) | HME Inhibition (%) |
|---|---|
| 0 | 0 |
| 0.01 | 10.8 +/− 2.0 |
| 0.05 | 44.9 +/− 0.4 |
| 0.1 | 62.4 +/− 1.8 |
| 0.5 | 89.5 +/− 0.5 |

EXAMPLE 6

Enhancement of Elastic Fiber Network in Mouse Bladder, Skin, and Blood Vessel Walls by Ingestible Treatment C57BL/6 female mice of age five (5) weeks were purchased from Taconic Farms (Germantown, N.Y.). Mice were housed in appropriately sized cages in an environmentally controlled room with a 12-hour light/12-hour dark photoperiod and supplied with food and water ad libitum. Animals were acclimated for three weeks before commencing the study. The animals were fed a special Casein Based Diet (5K96 with low isoflavone content, purchased from TestDiet (Richmond, Ind.) and housed together to achieve synchronized estrous cycling. After acclimation, 200 microliters of the unfiltered extract blend of Example 1E (Table 3) were given orally, once daily, five days a week (Monday through Friday). Skin and bladder samples following 12 weeks of treatment were obtained for histological analysis.

Three months after the start of the ingestible treatments, bladder and skin samples were analyzed histologically for elastin fibers. Surprisingly, an increased amount of elastic fibers was observed in mouse bladders and skins from mice treated with the extract, as compared to control (Table 11), based on the following grading: normal (Control)—+; slightly increased—++; and considerable increased—+++.

TABLE 11

|  | Bladder | N | Skin | N |
|---|---|---|---|---|
| Control | + | 2 out of 2 | + | 2 out of 2 |
| Malva sylvestris/ Matricaria chamomilla/ Cotinus coggygria | +++ | 2 out of 2 | ++ | 2 out of 2 |

The ingestible treatments were continued for additional two months, and bladder and skin samples at week 22 after the start of the treatments were analyzed histologically for elastin fibers. Surprisingly, an even greater increase in elastic fibers was observed in mouse bladders and skins from mice treated with the extracts, as compared to control and to results from week 12. Elastin fiber density around blood vessels within the bladder sections was also evaluated. As shown in Table 12, there was a considerable increase in the elastin fiber density in and around blood vessels in bladders of treated mice, as compared to controls. Results of 22-week treatment are shown in Table 12.

TABLE 12

|  | Bladder | N | Blood vessels | N | Skin | N |
|---|---|---|---|---|---|---|
| Control | + | 2 out of 2 | + | 2 out of 2 | + | 2 out of 2 |
| Malva sylvestris/ Matricaria chamomilla/ Cotinus coggygria | +++ | 2 out of 3 | +++ | 3 out of 3 | ++(+) | 3 out of 3 |

EXAMPLE 7

Improvement in Systemic Health Parameters by Ingestible Treatment

Mice treated as in Example 6 were also tested for the effect on mouse plasma triglyceride and uric acid levels. Three months after the start of the treatments, mice were sedated by isoflurane gas inhalation, and blood was collected by heart puncture. As shown in Table 13, a considerable decrease in the levels of triglycerides was observed in the sera of the mice treated with the selected natural extracts, as compared to controls.

TABLE 13

| Groups | Triglycerides mg/dl |
|---|---|
| Control | 87 +/− 3 |
| Treated | 51 +/− 6 |

Plasma levels of uric acid were determined in the sera of mice isolated as described above. As shown in Table 14, a considerable decrease in the levels of uric acid was observed in plasma from mice treated with the selected natural extracts, as compared to controls, 12 weeks after the start of the treatments.

The ingestible treatments were continued for additional two months, and mice were sedated by isoflurane gas inhalation, and blood was collected by heart puncture. As shown in Table 14, a considerable decrease in the levels of uric acid was observed in plasma from mice treated with the natural extracts, as compared to controls. Results of 12-week and 22-week treatments are shown in Table 14.

TABLE 14

| Groups | Uric acid mg/dl (12 weeks) | Uric acid mg/dl (22 weeks) |
|---|---|---|
| Control | 3.75 +/− 0.25 | 4.01 +/− 1.18 |
| Treated | 1.95 +/− 0.15 | 2.83 +/− 0.46 |

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of increasing the elasticity or structural integrity of skin, bladder tissue, blood vessel walls, or vaginal mucosal tissue of a mammal in need of treatment for sagging, lax, or loose tissue, said method comprising the ingestion by said mammal of a composition comprising an effective amount of an aqueous extract of *Cotinus coggygria* and an effective amount of aqueous extract of *Malva sylvestris* flowers.

2. The method of claim 1, wherein said method comprises increasing the elasticity or structural integrity of the skin.

3. The method of claim 1, wherein said method comprises increasing the elasticity or structural integrity of bladder tissue.

4. The method of claim 1, wherein said method comprises increasing the elasticity or structural integrity of vaginal tissue.

5. The method of claim 1, wherein said method comprises increasing the elasticity or structural integrity of blood vessel walls.

6. The method of claim 1, wherein said composition further comprises *Matricaria chamomilla* aqueous extract.

7. The method of claim 1, wherein said composition further comprises one or more extracts selected from the group consisting of *Arctostaphylos uva-ursi* aqueous extract, *Thymus vulgaris* aqueous extract, *Thymus serpyllum* aqueous extract, and *Matricaria recutita* aqueous extract.

8. The method of claim 6, wherein said composition further comprises one or more extracts selected from the group consisting of *Arctostaphylos uva-ursi* aqueous extract, *Thymus vulgaris* aqueous extract, *Thymus serpyllum* aqueous extract, and *Matricaria recutita* aqueous extract.

9. The method of claim 1, wherein said composition comprises an aqueous extract of the leaves of *Cotinus coggygria*.

* * * * *